United States Patent [19]
Butt et al.

[11] Patent Number: 5,430,212
[45] Date of Patent: Jul. 4, 1995

[54] OLEFIN OLIGOMERIZATION

[75] Inventors: Martin H. D. Butt, Ponca City, Okla.; Francis J. Waller, Allentown, Pa.

[73] Assignee: E. I. Du Pont de Nemours and Company, Wilmington, Del.

[21] Appl. No.: 202,607

[22] Filed: Feb. 28, 1994

Related U.S. Application Data

[62] Division of Ser. No. 47,395, Apr. 19, 1993, Pat. No. 5,315,033, which is a division of Ser. No. 788,389, Nov. 6, 1991, Pat. No. 5,233,102, which is a division of Ser. No. 388,400, Aug. 2, 1989, Pat. No. 5,094,995.

[51] Int. Cl.⁶ ................................................ C07C 2/08
[52] U.S. Cl. ...................... 585/526; 585/515; 585/520
[58] Field of Search ................ 585/510, 575, 520, 526

[56] References Cited

U.S. PATENT DOCUMENTS

| | | | |
|---|---|---|---|
| 3,282,875 | 11/1966 | Connelly et al. | 260/29.6 |
| 3,577,266 | 5/1971 | Kirkland | 117/100 |
| 4,038,213 | 7/1977 | McClure et al. | 585/500 |
| 4,065,512 | 12/1977 | Cares | 260/644 |
| 4,176,215 | 11/1979 | Molnar et al. | 521/27 |
| 4,303,551 | 12/1981 | Vaughan | 252/430 |
| 4,358,545 | 9/1982 | Ezzell et al. | 521/27 |
| 4,433,082 | 2/1984 | Grot | 524/755 |
| 4,470,859 | 9/1984 | Benezra et al. | 156/155 |
| 4,661,411 | 4/1987 | Martin et al. | 428/421 |
| 4,990,716 | 2/1991 | Schmidt et al. | 585/458 |

OTHER PUBLICATIONS

Waller et al., *Chemtech*, pp. 438–441 (Jul. 1987).
Martin et al., *Anal. Chem.*, 54(9):1639–1641 (Aug. 1982).
F. J. Waller *Polymeric Reagents and Catalysts*, A.C.S. Symposium Series 308, pp. 43–67, Washington, D.C. (1986).
F. J. Wallker, *Catal. Rev. Sci. Eng.* 28(1):1–12 (1986).

*Primary Examiner*—P. Achutamurthy

[57] ABSTRACT

A catalyst composition comprising a perfluorinated ion-exchange polymer containing sulfonic acid groups supported on an inert carrier having a hydrophobic surface with a mean pore diameter of at least 1000 Å. Use of this catalyst provides improved hydrocarbon conversion processes for oligomerization of olefins, hydration of olefins and hydrolysis of esters.

2 Claims, No Drawings

OLEFIN OLIGOMERIZATION

This is a division of application Ser. No. 08/047,395, filed Apr. 19, 1993, U.S. Pat. No. 5,315,033, which is a division of Ser. No. 07/788,389, filed Nov. 6, 1991, U.S. Pat. No. 5,233,102, which is a division of Ser. No. 07/388,400, filed Aug. 2, 1989, U.S. Pat. No. 5,094,995.

FIELD OF THE INVENTION

This invention relates to supported perfluorinated ion-exchange polymers, and to the use of the supported polymers in acid-catalyzed reactions.

BACKGROUND OF THE INVENTION

Perfluorinated ion exchange polymers with pendant sulfonic acid groups have been used in a wide variety of acid catalyzed reactions, including hydrocarbon conversion reactions such as acylation, carbonylation, condensation, alkylation and oligomerization. For a review, see Waller et al., Chemtech, July, 1987, pp 438–441, and references therein.

In these acid catalyzed reactions, the perfluorinated ion exchange polymers with sulfonic acid groups have been used in the form of powders, films, cubes, flakes and tubes. In general, the catalytic efficiency (amount of product divided by the amount of catalyst) of such polymers is related to surface area, so that the powders of polymers show higher activity than cubes in non-swelling solvents. However, fine particulate particles tend to exhibit poor flow dynamics and lead to plugging problems and loss of catalyst due to entrainment. Films and flakes are inconvenient forms to use in many large scale industrial processes. Perfluorinated ion exchange polymers containing sulfonic acid groups in the form of tubing have only a moderate surface area to weight ratio and are fragile and difficult to manufacture.

Perfluorinated ion exchange polymers with pendant sulfonic acid groups have also been coated on various supports to increase the number of acid sites available, providing catalysts with increased catalytic efficiency at a lower cost.

U.S. Pat. No. 4,661,411 discloses the preparation of a heterogeneous acid catalyst, which involves treating a carrier material with a solution, which contains a fluorinated polymer dissolved in a suitable solvent, such polymer having sulfonic acid functional groups; removing the solvent involved in the prior step; and heat treating or annealing the coated carrier in a fashion to prevent the polymer from being leached from the carrier. Aqueous ethanol, particularly 50% aqueous ethanol used at 250° C. or higher for several hours in an autoclave, is a suitable solvent for dissolving the unannealed fluorinated polymer. The composition of the carrier is not considered critical, and several, including carbon are suggested.

U.S. Pat. No. 4,038,213 discloses the preparation of a supported perfluorinated polymer catalyst by dissolving the polymer (a perfluorinated ion exchange polymer containing pendent sulfonic acid groups) in a solvent, such as ethanol, mixing the support and the catalyst solution, and then drying the impregnated support under vacuum. Disclosed supports or carriers have an average pore diameter of 50 to 600 Å and are inorganic oxides such as alumina, fluorided alumina, zirconia, silica, silica-alumina, magnesia, chromia, boria, and mixtures thereof; other suitable porous supports include bauxite, kieselguhr, kaolin, bentonite, diatomaceous earth, polytetrafluoroethylene, carbon (e.g., charcoal), polytrichlorofluoroethylene and porous glass. The supported catalyst is useful in hydrocarbon conversion reactions, e.g., alkylation of isoparaffins, isomerization of normal alkanes, disproportionation of toluene and the alkylation of benzene.

U.S. Pat. No. 4,303,551 discloses an improved process for making supported perfluorosulfonic acid catalyst, comprising converting the sulfonic acid groups to the quaternary ammonium or phosphonium salts to effect solubility of the polymers, depositing the polymer containing the quaternary ammonium or phosphonium salts on a support, then, converting the ammonium or phosphonium salts to the sulfonic acid. The ammonium or phosphonium salts are soluble in dipolar, aprotic solvents such as dimethylformamide and dimethyl sulfoxide. A process is also disclosed for preparing a supported perfluorocarbon polymer containing pendant acid groups by first coating the support with a thin film of a catalyst precursor containing pendant groups which are convertible to acid groups, and then converting only the surface layer of said pendant groups into acid groups. Suggested supports include metal, Teflon ® fibers, asbestos, glass, ceramics, sulfonyl fluoride polymers, and the perfluorocarbon sulfonyl fluoride itself.

In general, the supports have been chosen for their low cost, high surface area, inertness under the reaction conditions, mechanical strength or a combination of these factors. Little consideration has been given to the effect of the hydrophilic/hydrophobic nature of the support surface on the catalytic activity of the supported catalyst.

Quite unexpectedly, it has been found that catalysts obtained by coating perfluorinated ion exchange polymers with pendant sulfonic acid groups on supports with hydrophobic surfaces are significantly more active in acid-catalyzed reactions than similar catalysts prepared from supports with hydrophilic surfaces.

SUMMARY OF THE INVENTION

This invention provides improved hydrocarbon conversion processes which comprise contacting said hydrocarbons under hydrocarbon converting conditions with a catalyst composition comprising 0.05–3.0% by weight of a perfluorinated ion exchange polymer containing sulfonic acid groups supported on an inert carrier, wherein the surface of the carrier is hydrophobic and has a mean pore diameter of at least 1000 Å. The improved processes include oligomerization of olefins, hydration of olefins and hydrolysis of esters.

This invention also provides a novel catalyst composition comprising a perfluorinated ion-exchange polymer containing sulfonic acid groups supported on an inert carrier having a hydrophobic surface with a mean pore diameter of at least 1000 Å. In particular the carrier comprises calcined shot coke.

DETAILED DESCRIPTION OF THE INVENTION

The catalysts which are used in the processes of this invention are prepared by contacting the hydrophobic support with a solution of the sulfonic acid substituted perfluorinated ion exchange polymer, removing the excess solvent to give a coated support, and activating the coated support by treatment with a strong mineral acid to give the supported catalyst.

The polymers that are suitable for use in this invention have structures that include a substantially fluorinated carbon chain that may have attached to it side chains that are also substantially fluorinated, and contain sulfonic acid groups or derivatives of sulfonic acid groups. Such polymers for use in this invention have an equivalent weight of at least about 500. Preferably, the perfluorinated polymer contains a sufficient number of sulfonic acid groups to give an equivalent weight of from about 500 to about 20,000, and most preferably from about 900 to about 2,000. Although the polymer backbone comprises, for the most part, fluorinated carbon atoms, it is not necessary that all other atoms be excluded. For example, ether oxygen atoms may be present in the backbone, as well as in the side chains of the polymer. Such other atoms and/or groups as hydrogen (H), chlorine (Cl) and carboxy (COOH) may be present in limited amounts without significantly affecting the stability or operability of the polymer under process conditions. It is preferred that the polymer contain no greater than about 5 weight percent total of hydrogen and chlorine groups. Representative of the perfluorinated polymers suitable for use in the present invention are the Nafion ® polymers (a family of catalysts for use in the manufacture of industrial chemicals, commercially available from E. I. du Pont de Nemours and Company), and the polymers, or derivatives of polymers, disclosed in U.S. Pat. Nos. 3,282,875; 4,329,435; 4,330,654; 4,358,545; 4,417,969 and 4,610,762, which are hereby incorporated by reference.

Typically, suitable perfluorinated polymers are derived from sulfonylhalide group-containing polymers having a fluorinated hydrocarbon backbone chain to which are attached the functional groups or pendant side chains which in turn carry the functional groups. The pendant side chains can contain, for example,

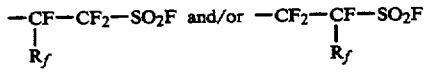

groups, wherein $R_f$ is F, Cl, or a $C_1$ to $C_{10}$ perfluoroalkyl radical. Ordinarily, the functional group in the side chains of the polymer will be present in terminal

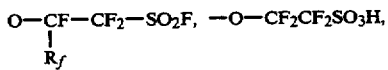

and/or

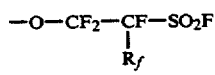

positions.

Although the fluorinated portion of the polymer molecule is in large part responsible for the desirable thermal stability of these polymers, it also contributes to the low solubility, and hence difficult processability, of these materials. However, it is possible to dissolve the polymer by heating it with an aqueous alcohol, particularly 50% aqueous ethanol, to about 250° C. or higher for several hours in a high pressure autoclave (Martin et al., Anal. Chem., Vol. 54, pp 1639–1641 (1982). Other solvents and mixtures may also be effective in dissolving the polymer. See, for example, U.S. Pat. No. 4,433,082.

Ordinarily, for each part by weight of polymer employed to be dissolved, from as little as about 4 or 5 parts by weight up to about 100 parts by weight, preferably 20–50 parts by weight, of the solvent mixture are employed. In the preparation of the dissolved polymer, there is an interaction between the equivalent weight of the polymer employed, the temperature of the process, and the amount and nature of the solvent mixture employed. For higher equivalent weight polymers, the temperature employed is ordinarily higher and the amount of liquid mixture employed is usually greater.

The resulting mixture may be used directly, but it is preferred that the mixture be filtered through fine filters (e.g., 4–5.5 micrometers) to obtain clear, though perhaps slightly colored, solutions. The mixtures obtained by this process can be further modified by removing a portion of the water, alcohols and volatile organic by-products by distillation.

Commercially available solutions of perfluorinated ion-exchange polymers can also be used in the preparation of the supported polymer catalysts of the present invention (e.g., a 5 wt. % solution of a perfluorinated ion-exchange powder in a mixture of lower aliphatic alcohols and 10% water, Cat. No. 27,470-4, Aldrich Chemical Company, Inc., 940 West Saint Paul Avenue, Milwaukee, Wis. 53233).

The polymer can be deposited on the support by soaking the support in the liquid mixture containing the polymer and then removing any excess solvent. Typically, the coated support is dried at a temperature above the boiling point of the solvents for at least 1 hour. Alternatively, the supported polymer can be prepared by atomizing the coating solution in air in a sonic velocity nozzle as in U.S. Pat. No. 4,430,001, herein incorporated by reference. Preferably, the supported polymer is prepared using a fluidized bed as detailed in the examples.

The thickness of the coating can be varied by adjusting the concentration of the polymer in the liquid mixture or by applying two or more layers of polymer onto the support. Suitable weight ratios of polymer-to-support vary from about 0.05 to about 3.0%. Higher weight ratios are possible, but less economic.

The composition of the support has been found to be important, however the properties that are considered most desirable for a carrier may vary in different applications. Properties that may be important in some situations include high surface area, high crush strength, high porosity, chemical resistance, thermal stability, and low cost. In all cases, the support must be resistant to the liquid composition of the polymer blend and to the temperatures used during the drying of the catalyst. For the catalysts used in the processes of this invention, it is also important that the surface of the support be hydrophobic. Preferred supports with hydrophobic surfaces include polytetrafluoroethylene, copolymers of polytetrafluoroethylene and hexafluoropropylene, polyethylene, polypropylene and carbon in the form of coke.

A specifically preferred support is coke. "Coke" as used herein is the non-volatile residue of petroleum refining or coal distillation operations. Its composition depends on the source of the feedstock and the processing methods used. In general, it has a high C:H ratio and contains condensed, polynuclear aromatic compounds as well as organic and inorganic compounds of sulfur, nitrogen and metals such as vanadium, nickel, iron and copper. Coke includes a very broad range of hydrophobic materials including tar pitch coke, coke oven coke, needle coke, regular grade or anode coke, fuel grade coke, shot coke, speciality carbon cokes such as gilsonite coke or others. Although the coke may be used in the green uncalcined form, it is preferable that the coke be calcined.

The most preferred support is calcined shot coke. Calcined shot coke alone is not a catalyst for hydrocarbon conversion reactions. The pore size range for conventional catalyst support material is between 50 and 600 Å. In contrast, the mean pore diameter in calcined shot coke is in excess of 1000 Å, and the average surface area is 0.1-10.0 m²/g. It is unusual that a material with such large pores provides an effective support medium for catalysis. Calcined shot coke also has a very high crush strength. The preferred loading for calcined shot coke is 0.05-3.0%; higher loadings are possible, but are less cost-efficient. Even coatings less than a monolayer thick of the polymer on the calcined shot coke result in a catalyst of high activity.

The supported perfluorinated ion-exchange polymers described herein can be used for hydrocarbon conversion reactions in continuous processes or in batch reactions.

Catalytic activity of the supported catalysts gradually decreases with use, but can be substantially restored by treatment with dilute acid, preferably 1N nitric acid, at about 80° C. In general, the integrity of the coated catalyst is maintained through many reaction cycles. The coating does not dissolve or flake off under the conditions of the hydrocarbon conversion reactions.

The oligomerization of olefins is one of many industrially important acid-catalyzed reactions. Known catalysts for the process include both homogeneous and heterogeneous, organic and inorganic, acids. Generally, heterogeneous catalysts are preferred because of the ease of their separation from the reaction mixtures.

The oligomerization of olefins involves the condensation of olefins to compounds of higher molecular weight. The distribution of oligomers between dimers, trimers, tetramers and higher molecular weight products depends both on the reaction conditions and the olefin starting material. Generally those olefins which can form relatively stable carbonium ions upon protonation oligomerize most easily. Rearrangements of the condensed products also occur frequently, especially for highly substituted olefins. The oligomerization of olefins is useful for the conversion of low molecular weight, often gaseous, hydrocarbons to higher molecular weight liquid or solid products. In particular, low molecular weight materials can be converted to blending components for gasoline.

In one process of this invention, the oligomerization of olefins is carried out by contacting at about 135° C. to 185° C. an olefin chosen from the group of monoolefins containing 3 or more carbons with a catalyst composition comprising 0.05-2.0 weight percent of a perfluorinated ion exchange polymer containing sulfonic acid groups supported on the surface of an inert support having a hydrophobic surface with a mean pore diameter of about 1000 Å. Preferably, the inert support is calcined shot coke.

In another process of this invention, the hydrolysis of esters is carried out by contacting in the presence of water and at a temperature of from about 75° C. to about 225° C., an ester chosen from the group consisting of esters of $C_3$ to $C_8$ dicarboxylic acids with a catalyst composition comprising 0.05-2.0 weight percent of a perfluorinated ion exchange polymer containing sulfonic acid groups supported on the surface of an inert support having a hydrophobic surface with a mean pore diameter of about 1000 Å. Preferably, the temperature is from about 130° C., to about 180° C. and the ester is chosen from the group consisting of mono- or dimethyl adipate or mono- or dimethyl glutarate. Most preferably, the inert support is calcined shot coke and the ester is dimethyl adipate.

The hydration of olefins to convert hydrocarbons to alcohols industrially important reaction that is often difficult to catalyze. In another process of this invention, the hydration of olefins is carried out by contacting in the presence of water and at a temperature of about 180° C. to about 250° C., an olefin chosen from the group of monoolefins containing 2 or more carbon atoms and a catalyst composition comprising 0.05-2.5 weight percent of a perfluorinated ion exchange polymer containing sulfonic acid groups supported on an inert support having a hydrophobic surface with a mean pore diameter of about 1000 Å. Preferably, the olefin is chosen from the group of $C_2$ to $C_{20}$ monoolefins, the temperature is about 200° C. to about 240° C. and the olefin is in the gas phase. Most preferably, the olefin is ethylene, propylene, isobutylene or 1-butene and the inert support is calcined shot coke.

EXAMPLES

The following Examples are presented for the purpose of illustration and are not in any way to be construed as limiting the scope of the invention as described herein.

Example 1

Example 1 illustrates the preparation of a perfluorinated ion exchange polymer containing sulfonic acid groups on a calcined shot coke support. A liquid composition of such a perfluorinated polymer (100 mL of a 5 weight percent solution of polymer having an equivalent weight of 1100 in a mixture of lower aliphatic alcohols and 10% water, Aldrich Chem. Co., Cat. No. 27,470-4) was added to calcined shot coke (400 g, 10-20 mesh, 0.42 m²/g). The coated catalyst was rotated occasionally for 0.5 hour and then the small amount of nonadsorbed solution was decanted off. The coated coke was dried at 80° C. for 1.5 h in vacuo. This coating procedure was repeated with another 100 mL of the liquid composition of the polymer, which was completely adsorbed. The coated coke was thoroughly dried in a vacuum oven for 12 hours at 110° C. The resulting coated shot coke weighed 407 g. The dried, coated coke was treated with dilute $HNO_3$ (approx. 1M, 860 mL) for 1 hour at 80° C. to convert the functional groups to sulfonic or carboxylic acid groups. The activated catalyst was washed with 300 mL of distilled water and dried in a vacuum oven at 110° C. for 3 hours.

The dried and activated catalyst was titrated with NaOH by adding a 1.59 g portion of the catalyst to 20 mL of water containing 1.0 g of NaCl and 3 drops of 1% phenolphthalein in methanol. The pink color of the indicator persisted for 5 minutes after 2.85 mL of $10^{-2}$N NaOH was added, implying that the ion-exchange capacity (hereinafter IEC) is $17.92 \times 10^{-3}$ mequiv/g. Similarly, the IEC of the uncoated CSC was determined to be $0.24 \times 10^{-3}$ mequiv/g. This implies a corrected IEC for the coated support of $17.68 \times 10^{-3}$ mequiv/g, corresponding to a 1.94% loading (based on IEC=0.909 mequiv/g of the polymer).

Examples 2-3

Examples 2 and 3 were prepared as described for Example. 1, using the reagent quantities summarized in Table 1.

TABLE 1

| | | Preparation of Catalyst | | |
|---|---|---|---|---|
| Example Number | Calcined Shot Coke | Polymer Solution | Corrected IEC mequiv/g × $10^3$ | Loading % |
| 1 | 400 g 10-20 mesh | 2 × 100 mL (5 wt. %) | 17.68 | 1.94 |
| 2 | 174 g >10 mesh | 40 mL (5 wt. %) + 20 mL MeOH | 4.58 | 0.57 |
| 3 | 159 g >10 mesh | [40 ml (5 wt. %) + 20 mL MeOH] + [40 mL (5 wt. %) + 20 mL MeOH] | 8.33 | 0.92 |

Examples 4-6

Examples 4-6 illustrate the oligomerization of isobutylene. A quartz equivalent of a Fisher-Porter tube was charged with isobutylene (15.0 g), toluene (15 mL), chlorobenzene (1.0 g, internal standard) and catalyst from Examples 1-3 respectively, and heated to 110° C. for 35 min. The products were analyzed by gas chromatography using a flame detector, a 0.31 mm (i.d.)×25 m column packed with cross-linked methyl silicone, and He gas at 20 mL/min. The temperature was held at 40° C. for 2 min, increased to 180° C. at a rate of 16° C./min, and held at 180° C. for 5 min.

The results of the oligomerization reactions are summarized in Table 2 for the catalysts of Examples 1-3 and comparative catalysts A-E.

TABLE 2

| | | Oligomerization of Isobutylene | | | |
|---|---|---|---|---|---|
| Example | Catalyst Example Number | Loading % | IEC/lb.$^d$ × $10^{-3}$ | Productivity$^a$ | Activity$^b$ × $10^{-3}$ |
| 4 | Ex. 1 | 1.94 | 8.03 | 1401 | 174 |
| 5 | Ex. 2 | 0.57 | 2.08 | 341 | 164 |
| 6 | Ex. 3 | 0.92 | 3.78 | 599 | 158 |
| | Comparative Example | | | | |
| A | Amberlyst 15 | — | 2130 | 1510 | 0.71 |
| B | PFIEP-SO$_3$H$^e$ 10-35 mesh | — | 360 | 669 | 1.86 |
| C | Calcined shot coke (10-20 mesh) | — | — | N.R. | — |
| D | XU-40036.01$^c$ | 14 | 63.6 | 1252 | 19.69 |
| E | XU-40035.01$^c$ | 22 | 99.9 | 900 | 9.01 |

$^a$Productivity = (Moles of C4 reacted)(lb. catalyst)$^{-1}$(hour)$^{-1}$
$^b$Activity = (Moles of C4 reacted)(IEC)$^{-1}$(hour)$^{-1}$
$^c$XU-40036.01 and XU-40036.02 are examples of fluorocarbonsulfonic acid polymers on α-alumina and silicon carbide, respectively (Dow Chemical Co.)
$^d$IEC is in "equivalents".
$^e$PFIEP-SO$_3$H is perfluorinated ion-exchange polymer containing sulfonic acid groups.

Examples 7-13

Examples 7-13 illustrate the hydrolysis of dimethyl adipate. The initial charge of 100 mL H$_2$O, 12 g dimethyl adipate (DMA) and 20 g catalyst (0.5% Nafion ® on calcined shot coke prepared as in Example 1) was heated in an autoclave reactor to 160° C. or 180° C. A small agitator was rotated at 300 rpm. A total of 100 mL H$_2$O was pumped into the autoclave during 1 or 2 hours reaction period while venting out water and methanol at the same rate as water was pumped in. After the end of the reaction period (1-4 hours), the contents of the autoclave were cooled to about 90° C. and the catalyst separated by filtration for use in further experiments. The major products were adipic acid (AA) and mono-methyl adipate (MMA).

TABLE 3

| | | | | Hydrolysis of Dimethyl Adipate | | |
|---|---|---|---|---|---|---|
| | | | H$_2$O pumped in | Product Composition (Water Free Basis), % by weight | | |
| Ex. | Temp. °C. | Reaction Time, h | (= vented out) (mL) | DMA | MMA | AA |
| 7 | 160 | 2 | 205 | 0.74 | 11.6 | 86.8 |
| 8 | 160 | 4 | 200 | 0.14 | 0.22 | 99.1 |
| 9 | 160 | 2 | 200 | 0.36 | 11.6 | 87.2 |
| 10 | 160 | 1 | 200 | 0.99 | 31.3 | 66.0 |
| 11 | 160 | 1 | 200 | 1.22 | 3.6 | 93.9 |
| 12 | 180 | 2 | 200 | 0.18 | 0.39 | 99.1 |
| 13 | 180 | 2 | 100 | 0.45 | 0.82 | 98.4 |

Examples 14-16 and Comparative Example F

These examples illustrate the hydration of ethylene and propylene. A synthetic gas mixture of ethylene (7.5%), propylene (3.0%) and the balance hydrogen and methane was heated to 220° C. or 235° C., bubbled through water to attain a humidity level of about 75% of saturation at the give temperature and then fed into a Cat Poly Lab Reactor which contained Nafion ® (Comparative Example F) or calcined shot coke coated with Nafion ® prepared as in Example 1 (2.5-2.9 weight percent). The major products were ethanol and isopropanol. In this example, use of supported Nafion ® is much less costly than use of Nafion ® and is therefore advantageous.

TABLE 4

| | | | % Conversion | |
|---|---|---|---|---|
| Ex. | Catalyst Loading | Temp. (°C.) | C2 to Ethanol | C3 to Isopropanol |
| 14 | 2.5% | 220 | 3.5 | 4.7 |
| 15 | 2.9% | 220 | 3.9* | 2.9* |
| 16 | 2.5% | 235 | 5.7 | 4.0 |
| F  | —    | 235 | 5.8 | 4.7 |

Hydration of Ethylene and Propylene (table heading)

*Run interrupted by power failures, and aborted prematurely. Conversion data are only estimates.

Example 17

A liquid composition of perfluorinated ion exchange polymer containing sulfonic acid groups as used in Example 1 (4500 g of 11.8% solution of polymer of 1100 equivalent weight) in a mixture of lower aliphatic alcohols and 40% water, was sprayed onto a fluidized air-suspended bed of calcined shot coke (15 kg, 35–60 mesh) at 25° C. The material was dried by the air flow within the fluidized bed until the moisture content was <0.1%. The final weight of the coated shot coke was 15.4 kg. The resulting coated coke was treated with dilute $HNO_3$ (approximately 2.4M) for 1 h at 85° C. to convert the functional groups to sulfonic acid groups. The activated catalyst was washed with distilled water and dried in a vacuum oven at 110° C. for 3 h.

The dried and activated catalyst was titrated with NaOH by adding a 1.50 g portion of the catalyst to 20 mL of water containing 1.0 g of NaCl and 5 drops of bromothymol blue indicator in methanol. The blue color of the indicator persisted for 10 min after 3.68 mL of 0.01N NaOH was added, implying that the ion-exchange capacity (IEC) was $24.53 \times 10^{-3}$ mequiv/g. The corrected IEC for the coated support was $24.29 \times 10^{-3}$, corresponding to a loading of 2.67%.

Example 18

The composition of materials and the method used were the same as that in Example 17, except that the temperature of the fluidized bed was kept at 60° C. The final weight of the coated shot coke was 15.3 kg. After treatment with dilute $HNO_3$, washing and drying, the catalyst was titrated with 2.76 mL of NaOH as in Example 17. The IEC was $18.40 \times 10^{-3}$ mequiv/g, corrected to 18.16 mequiv/g at a loading of 2.02%.

Example 19

The oligomerization of isobutylene was carried out as in Examples 4–6 using the supported catalyst of Examples 17 and 18. The results obtained are summarized in Table 5.

TABLE 5

Oligomerization of Isobutylene

| Catalyst Example Number | Loading wt. % | IEC/lb$^a$ $\times 10^{-3}$ | Productivity$^b$ $\times 10^{-3}$ | Activity$^c$ |
|---|---|---|---|---|
| 17 | 2.67 | 11.01 | 1266 | 115 |
| 18 | 2.02 | 8.34  | 700  | 84  |

$^a$IEC is in "equivalents"
$^b$Productivity = (moles of $C_4$ reacted)(lb catalyst)$^{-1}$(hour)$^{-1}$
$^c$Activity = (moles of $C_4$ reacted)(IEC)$^{-1}$(hour)$^{-1}$

What is claimed is:

1. An improved process for oligomerization of olefins wherein the improvement comprises contacting said olefins with a catalyst composition comprising a perfluorinated ion-exchange polymer containing sulfonic acid groups supported on an inert carrier wherein said carrier comprises calcined shot coke and has a hydrophobic surface with a mean pore diameter of at least 1000 Å; at a temperature of from about 135° C. to about 185° C.

2. The process of claim 1 wherein the olefin is isobutylene.

* * * * *